Figure 1:
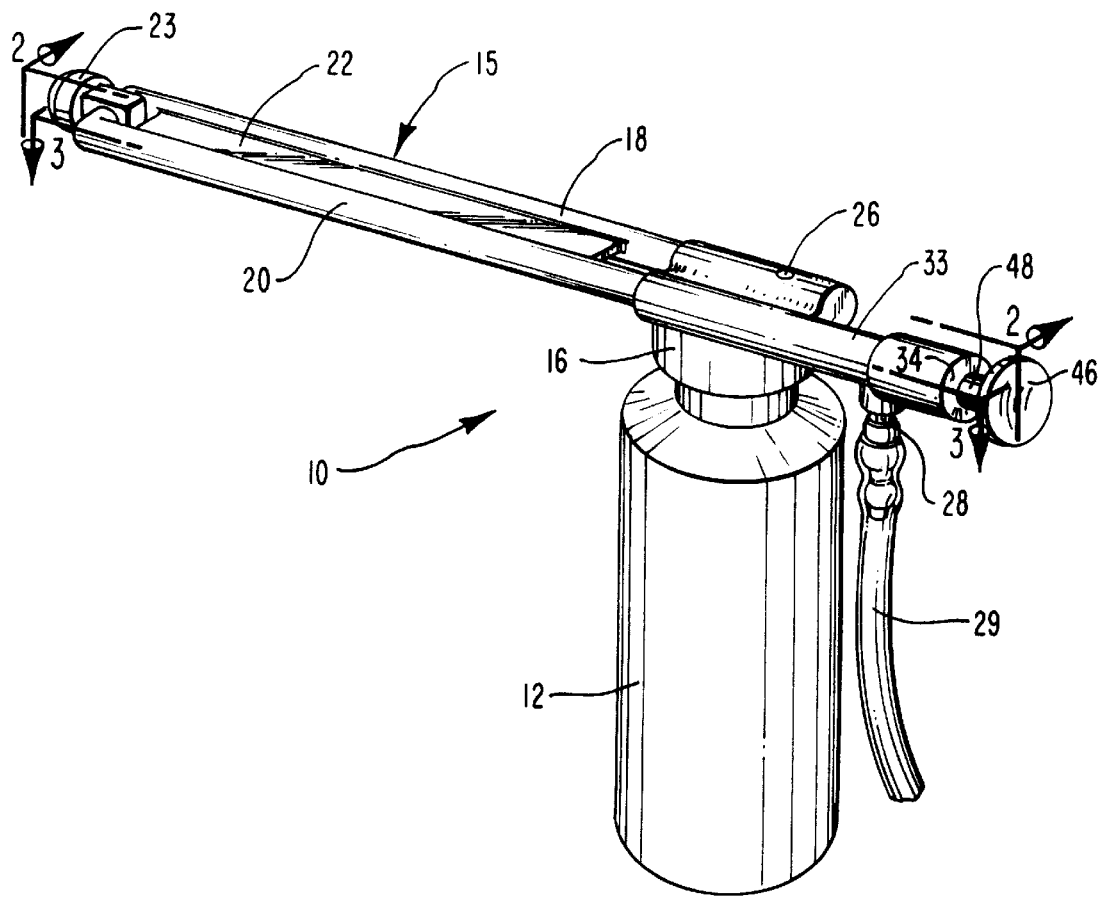
Figure 2:
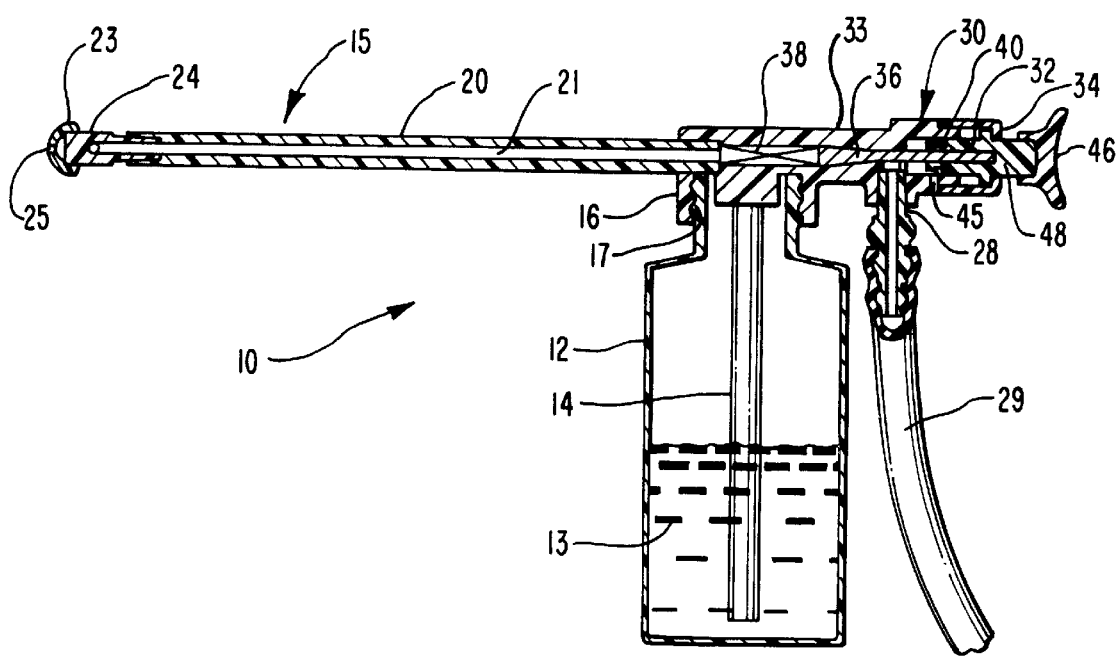
Figure 3:
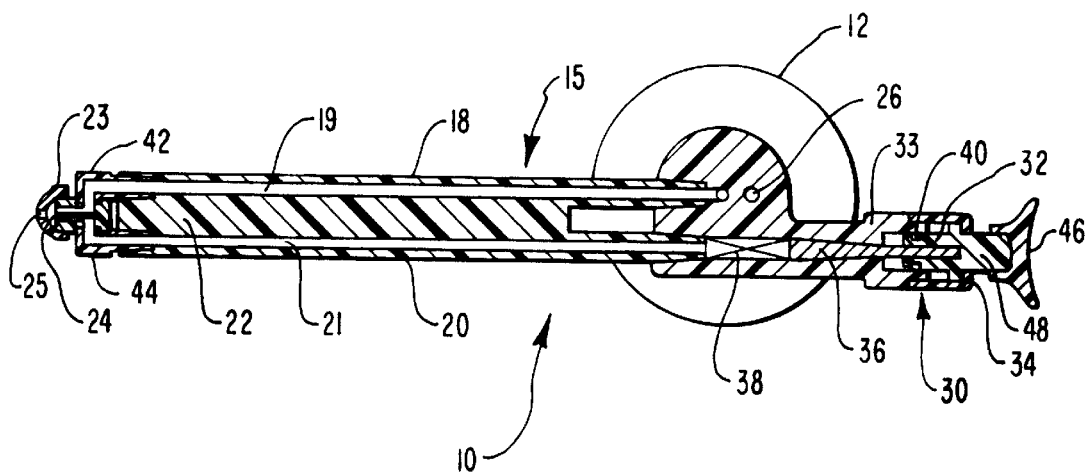

United States Patent

Allred et al.

[11] Patent Number: 6,021,776
[45] Date of Patent: Feb. 8, 2000

[54] DISPOSABLE ATOMIZER DEVICE WITH TRIGGER VALVE SYSTEM

[75] Inventors: George Allen Allred, Salt Lake City; Leland J. Coleman, Highland, both of Utah; John K. Bullock, Houston; Cecil C. Brewer, Missouri City, both of Tex.

[73] Assignees: Intertex Research, Inc., Houston; The Board of Regents of the University of Texas System, Austin, both of Tex.

[21] Appl. No.: 08/926,341

[22] Filed: Sep. 9, 1997

[51] Int. Cl.⁷ ................................................. A61M 11/00
[52] U.S. Cl. ................................ 128/200.21; 128/200.14
[58] Field of Search .................... 128/200.14, 200.21; 137/892; 239/318, 407

[56] References Cited

U.S. PATENT DOCUMENTS

| | | | |
|---|---|---|---|
| D. 303,139 | 8/1989 | Morgan | D23/223 |
| D. 333,000 | 2/1993 | Good et al. | D24/108 |
| 442,785 | 12/1890 | Schoettl | 128/200.14 |
| 460,458 | 9/1891 | Bates | 128/200.14 |
| 533,489 | 2/1895 | Ogram | 128/200.14 |
| 904,149 | 11/1908 | Rachmann | 128/200.14 |
| 938,648 | 11/1909 | DeVilbiss . | |
| 1,261,503 | 4/1918 | Figgis . | |
| 1,357,452 | 11/1920 | Hall | 239/348 |
| 1,466,119 | 8/1923 | Claflin | 239/417.5 |
| 2,004,402 | 6/1935 | Conklin | 128/200.14 |
| 2,390,313 | 12/1945 | Macgill | 222/74 |
| 2,934,314 | 4/1960 | Chambers et al. | 251/331 |
| 2,956,579 | 10/1960 | Moore et al. | 137/218 |
| 3,050,261 | 8/1962 | Littlefield | 239/318 |
| 3,599,866 | 8/1971 | Bolton | 239/8 |
| 3,632,046 | 1/1972 | Hengesbach | 239/318 |
| 3,647,143 | 3/1972 | Gauthier et al. | 128/200.14 |
| 3,649,299 | 3/1972 | Sholl | 128/200.14 |
| 3,762,410 | 10/1973 | Bindel | 128/200.14 |
| 3,815,595 | 6/1974 | Bar | 128/200.14 |
| 3,916,896 | 11/1975 | Ballard | 128/200.14 |
| 4,174,811 | 11/1979 | Binder et al. | 239/308 |
| 4,204,539 | 5/1980 | Van Brugge | 128/200.14 |
| 4,606,501 | 8/1986 | Bate et al. | 239/346 |
| 5,053,000 | 10/1991 | Booth et al. | 128/200.14 |
| 5,165,604 | 11/1992 | Copp, Jr. | 239/106 |
| 5,392,992 | 2/1995 | Farnsteiner et al. | 239/296 |

OTHER PUBLICATIONS

Product Literature for DeVilbiss Atomizers, "The Surgical Armamentarium" catalog, V. Mueller, Division of American Hospital Supply Corporation (1973).

*Primary Examiner*—Aaron J. Lewis
*Attorney, Agent, or Firm*—Workman, Nydegger & Seeley; Gregory M. Taylor

[57] ABSTRACT

A disposable atomizer device for directing a liquid into or on the body of a patient. The atomizer device includes a container for holding a liquid, and a liquid inlet tube disposed in the container. An atomizing nozzle is in communication with the liquid inlet tube. A gas inlet tube is in communication with the nozzle and is attachable to a source of compressed gas. The atomizer device includes a trigger valve system adjacent to the gas inlet tube for providing controlled release of compressed gas from the gas inlet tube to the atomizing nozzle. The trigger valve system includes a needle valve positioned in a needle support surrounded by a valve housing with a cap. The needle support is movably engaged with the cap for retaining the needle valve within the valve housing, and the needle valve is resiliently biased toward the cap. The valve housing has a pressure relief port for reducing line pressure to an acceptable level. When the needle support is depressed inwardly by an operator, the needle valve releases compressed gas from the gas inlet tube into the nozzle, thereby withdrawing the liquid from the container into the nozzle such that the liquid is atomized when discharged from the nozzle.

37 Claims, 2 Drawing Sheets

DISPOSABLE ATOMIZER DEVICE WITH TRIGGER VALVE SYSTEM

BACKGROUND OF THE INVENTION

1. The Field of the Invention

The present invention relates generally to atomizer devices for use in discharging a liquid into or on the body of a patient. More particularly, the present invention relates to a disposable atomizer device that includes a trigger valve system for enhanced control of a spray discharged from the atomizer device into or on the body of a patient.

2. The Relevant Technology

Atomizer devices have been in use for many years in order to create a spray from a reservoir of a liquid. Early atomizer devices, such as those disclosed in U.S. Pat. No. 938,648 to DeVilbiss, included a receptacle for a liquid that was attached to an air tube and a liquid tube. The air tube and the liquid tube communicated at their outer ends with a common spray head. A venturi effect was created by the spray head such that liquid was withdrawn from the receptacle through the liquid tube as air was passed through the air tube, thereby forming a spray discharged from the atomizer. Another early atomizer device, disclosed in U.S. Pat. No. 1,261,503 to Figgis, included a similar structure of a receptacle for a liquid attached to air and liquid tubes. A common spray head was swingingly mounted on the forward ends of the tubes and created a venturi effect for atomizing a liquid discharged from the device. While these early atomizers produced a liquid spray, there was no mechanism for controlling the air flow to the atomizer and the spray thereby produced.

Various other spray devices have been developed in the past that utilize a variety of complicated valve structures, pulling valves, and the like, to control air entry into the spray device. These include various spray guns used for paint, inhalers for medical treatment, and other such spray devices. Nondisposable reusable atomizer devices for medical use that utilize a venturi effect are available from Carabelly of Italy, and DeVilbiss Health Care, Inc., but these devices are expensive to use and replace.

The nondisposable atomizer device available from Carabelly (hereinafter the "Carabelly atomizer") is a portable device that includes a metal outlet tube containing two inner tubes for air and liquid, and a glass bottle for holding a liquid to be atomized. A rubber bulb connected to the device is squeezed by an operator in order to supply air to the device to generate a spray of the liquid.

A nondisposable atomizer device manufactured by DeVilbiss Health Care, Inc. (hereinafter the "DeVilbiss atomizer") includes a glass receptacle for holding a liquid, and a pair of metal outlet tubes extending from a metal coupler to an atomizing nozzle, with the coupler removably attached to the receptacle. One outlet tube communicates with the liquid in the receptacle via a glass inlet tube disposed in the receptacle. The other outlet tube communicates with a source of compressed air via a removable T-shaped metal connector having a bleeder port. In order to operate the DeVilbiss atomizer, the bleeder port in the T-shaped metal connector is covered by the operator to actuate compressed air flow to the nozzle. Such a configuration provides difficulty to an operator in regulating the air flow and the resulting spray discharged from the device, and the T-shaped connector can easily become dislodged from the device. Furthermore, the open aperture of the T-shaped connector can be a source of infection introduction to the patient, and can cause the operator to contract a sore or ulcer on a thumb or finger due to airborne contaminants.

The metal components in the Carabelly atomizer and the DeVilbiss atomizer are relatively difficult to manufacture, resulting in expensive products. Since these atomizers are nondisposable and reusable, it is necessary to disinfect and sterilize the devices after each use, which if not done properly increases the risk of spreading infection or disease.

Another problem that occurs with the above nondisposable metal-containing atomizer devices is that the medication atomized by such devices crystallizes on the inner surfaces of the metal components of the devices. This makes it very difficult, if not impossible, to clean these devices after repeated use, and often operators have to throw an expensive reusable atomizer device away and get a new device since the reused device becomes inoperable. In addition, it is difficult to maintain a quality control program in processing and cleaning reusable atomizers, and there is no quality control procedure incorporated in the cleaning cycle to ensure that the device is working properly. Thus, the operator never knows if the device is clogged or if it will function properly until the attempt is made to operate the device.

Further, the cleaning process for reusable atomizers is time-consuming and complicated. It takes approximately sixty minutes to clean and process a reusable atomizer device and prepare the device for reuse. The following steps are necessary to process a used atomizer device in order to ensure proper cleaning from one patient to the next. First, the device is soaked in a disinfecting agent after use, and then is transported to a central supply area for reprocessing. The device is then disassembled, hand cleaned, packaged, and placed in a sterilizer such as an autoclave. A problem that occurs in attempting to clean a used atomizer device is that the inner lumen of the device for the liquid medication is usually impossible to clean and becomes plugged after about two or three uses, resulting in a new device having to be used.

Accordingly, there is a need for an improved atomizer device for medical use that overcomes or avoids the problems of prior atomizer devices.

SUMMARY AND OBJECTS OF THE INVENTION

The present invention is directed to a disposable atomizer device for directing a liquid into or on the body of a patient. The atomizer device comprises a means for holding a liquid, such as a container, an atomizing nozzle in communication with the liquid holding means, and a means for supplying a compressed gas, such as air or oxygen, to the atomizing nozzle. A trigger valve system in the atomizer device provides controlled release of the compressed gas to the atomizing nozzle. The trigger valve system includes a needle valve strategically positioned in a needle support surrounded by a valve housing with a retainer cap. The needle support is movably engaged with the cap for retaining the needle valve within the valve housing, and the needle valve is resiliently biased toward the cap. A pressure relief port is also provided in the valve housing to permit proper gas-flow settings to be made prior to the actual atomizing of the liquid.

In a preferred embodiment, a liquid inlet tube is disposed in the container of the atomizer device, and a liquid outlet tube provides communication between the liquid inlet tube and the atomizing nozzle. A gas inlet tube adjacent to the trigger valve system is releasably attachable to a source of compressed gas. A gas outlet tube provides communication between the gas inlet tube and the atomizing nozzle via the needle valve. The needle valve is resiliently biased toward the cap by a suitable compression spring. In addition, the atomizing nozzle is pivotably attached to the atomizer device, and a flow control push-button is formed at an outer end of the needle support.

In a method of operating the atomizer device of the invention for directing a liquid into or on the body of a patient, a source of compressed gas is attached to the atomizer device, and the nozzle of the atomizer device is placed in a preselected position in or near the body of a patient. The needle support of the atomizer device is depressed inwardly with the push-button such that the needle valve releases the compressed gas from the inlet tube for passage to the atomizing nozzle. The passage of compressed gas through the nozzle withdraws the liquid into the nozzle by a venturi effect such that the liquid is atomized when mixed with compressed gas in the nozzle. The atomized liquid is then discharged in the form of a spray into or on the body of the patient.

Accordingly, a principal object of the present invention is to provide an atomizer device for medical use having enhanced control of gas flow to improve control over the spray discharged from the device.

Another object of the present invention is to provide an atomizer device that is a closed system which prevents spreading infection to both the operator and the patient.

Another object of the present invention is to provide an atomizer device for medical use that is disposable.

A further object of the present invention is to provide an atomizer device for medical use that can be produced less expensively than prior atomizers.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 1 is a perspective view of an atomizer device according to the present invention;

FIG. 2 is a cross-sectional side view of the atomizer device shown in FIG. 1 taken along line 2—2 of FIG. 1;

FIG. 3 is a cross-sectional overhead view of the atomizer device shown in FIG. 1 taken along line 3—3 of FIG. 1; and FIG. 4 is an enlarged cross-sectional side view of the trigger valve system of the atomizer device shown in FIG. 2.

DETAILED DESCRIPTION OF THE INVENTION

The present invention is directed to a disposable atomizer device for directing a liquid into or on the body of a patient. The atomizer device includes a novel trigger valve system providing controlled release of compressed gas to an atomizing nozzle to create a liquid spray that is effectively controllable by an operator. The device of the present invention can be used in medical applications to treat a human patient, or can be used in veterinary medicine to treat an animal.

Referring to FIGS. 1 and 2, an atomizer device 10 according to the present invention is depicted. The atomizer device 10 includes a liquid holding means, such as a container 12 for holding a liquid 13 that can include one or more medicaments for treating a patient. It will be appreciated that the liquid holding means can be implemented using various other equivalent structures and be within the intended scope of the invention. For example, a variety of differently sized and shaped receptacles, bottles, or containers can be utilized for holding a liquid medication to be sprayed into or on the body of a patient by atomizer device 10.

A liquid inlet tube 14 is disposed within container 12 and communicates with a discharge section 15 of atomizer device 10. The container 12 is attached at the inlet end thereof to discharge section 15 by a coupling means for detachably coupling container 12 to discharge section 15. One presently preferred embodiment of the coupling means includes a coupling portion 16 on discharge section 15, with coupling portion 16 having female threads on the inner surface thereof that are complementary with male threads on the outer surface of a threaded neck portion 17 of container 12.

It will be appreciated that the coupling means can be implemented using various other equivalent structures and be within the intended scope of the invention. For example, coupling portion 16 can be formed with male threads and threaded neck portion 17 can be formed with complementary female threads. In addition, container 12 can be detachably coupled to discharge section 15 by way of a Luer-lock type attachment in which container 12 utilizes a female Luer connector and coupling portion 16 uses a male Luer connector or vice versa. Any other arrangement can be used known to those skilled in the art wherein container 12 detachably couples to discharge section 15. In an alternative embodiment, container 12 can be permanently attached to discharge section 15 of atomizer device 10 by various adhesive or ultrasonic welding techniques known to those skilled in the art.

The coupling portion 16 has a negative pressure relief opening 26 extending therethrough from the upper surface of atomizer device 10 to the interior of container 12. The pressure relief opening 26 can be used by an operator to modify or regulate the spray pattern and vary the droplet size by covering opening 26 with a finger.

The discharge section 15 includes a liquid outlet tube 18 and a gas outlet tube 20 that extend substantially parallel to each other in a perpendicular direction from container 12. An elongated flange 22 connects liquid outlet tube 18 to gas outlet tube 20 to provide stability to discharge section 15. The liquid outlet tube 18 provides communication between liquid inlet tube 14 and an atomizing nozzle 23, while gas outlet tube 20 provides communication between a source of compressed gas (not shown) and atomizing nozzle 23.

As shown in FIGS. 2 and 3, liquid outlet tube 18 defines a liquid channel 19, and gas outlet tube 20 defines a gas channel 21. The liquid channel 19 is in communication at aproximal end thereof with liquid inlet tube 14 disposed in container 12. The gas channel 21 is in communication at a proximal end thereof with a means for supplying compressed gas, such as a gas inlet tube 28, via a trigger valve system 30 discussed in greater detail below. As shown, the gas inlet tube 28 is configured to be a universal connector allowing attachment of a connecting tube 29 which can be of different sizes. The connecting tube 29 provides communication between a source of compressed gas and gas inlet tube 28. The gas supplied under compression can be dry air, oxygen, nitrogen, an inert gas, and the like. The compressed gas selected for use with atomizer device 10 depends on the application for which the device is being used.

The atomizing nozzle 23 is pivotably attached to liquid outlet tube 18 and gas outlet tube 20 at the distal ends thereof through pivot arms 42 and 44, which provide communication between channels 19, 21 and a venturi section 24 of nozzle 23. The venturi section 24 of atomizing nozzle 23 creates a negative pressure effect when compressed gas is passed through channel 21 into nozzle 23, thereby withdrawing liquid 13 from container 12 through liquid inlet tube 14 and into liquid outlet tube 18. The gas channel 21 is appropriately sized and passes through venturi section 24 to create the negative pressure that is exerted on liquid channel 19 through which liquid 13 is drawn when compressed gas travels through channel 21. The liquid 13 mixes with the compressed gas in nozzle 23, thereby creating a spray that is discharged from an outlet aperture 25 of nozzle 23. The pivotal attachment of nozzle 23 to liquid outlet tube 18 and gas outlet tube 20 allows nozzle 23 to be adjusted and positioned at various angles so that the spray can be directed as desired.

Figure 4:
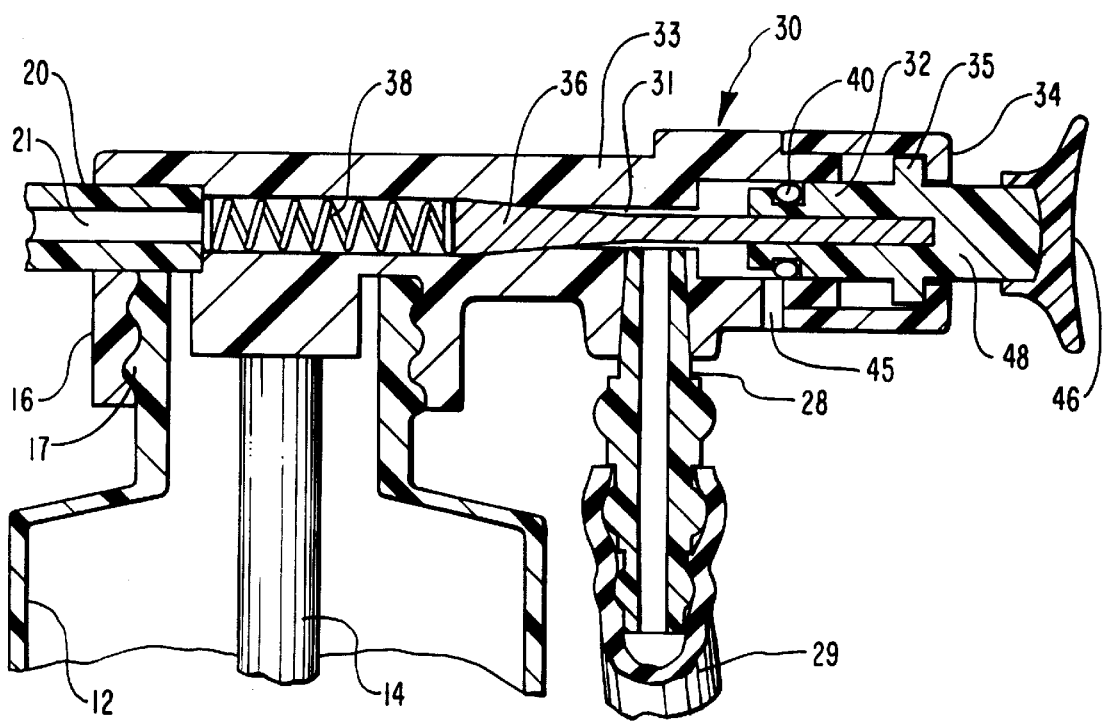

FIG. 4 is an enlarged cross-sectional view of the trigger valve system 30 used in the atomizer device of the present invention to provide controlled release of compressed gas to atomizing nozzle 23. The trigger valve system 30 is positioned adjacent to gas inlet tube 28 in order to control the flow of compressed gas into channel 21 via a conical valve channel 31. The trigger valve system 30 includes a valve housing 33 integrally formed with coupling portion 16 and defining valve channel 31. A needle support 32 is movably engaged with a retainer cap 34 at the reward end of valve housing 33. A needle valve 36, which tapers to an increased outer diameter at its distal end, is positioned in and extends from needle support 32. The needle valve 36 extends inwardly past gas inlet tube 28 into valve channel 31 and outwardly toward gas outlet tube 20. A protruding flange 35 formed on the outer surface of needle support 32 interacts with the interior surface of cap 34 and abuts against a shoulder portion of cap 34 to retain a portion of needle support 32 within cap 34. The remaining portion of needle support 32 extends rearwardly through an opening in cap 34 and into a thumb pad 46 to form a flow control push-button 48 exterior of valve housing 33 that can be depressed by an operator. The interaction of needle support 32 and cap 34 thus retain needle valve 36 within the interior of valve housing 33. The needle valve 36 essentially acts like a plunger that releases compressed gas when moved inwardly, and needle valve 36 loosely fits in valve channel 31 to allow ease of movement.

A resilient bias means for urging needle valve 36 and needle support 32 toward the rearward end of retainer cap 34 is provided in trigger valve system 30. As shown in FIG. 4, the resilient bias means can be a compression spring 38 positioned within coupling portion 16 above container 12 in front of needle valve 36 such that needle support 32 is spring loaded. The spring 38 compresses when needle support 32 is depressed inwardly, thereby providing a sufficient force to return needle valve 36 to a sealed condition when push-button 48 is released by an operator. In addition, it will be appreciated that needle valve 36 can be resiliently biased toward the rearward end of cap 34 by other resilient bias means known to those skilled in the art, such as by pneumatics, fluidics, and the like.

An O-ring 40 is disposed around an outer circumference of needle support 32 toward a distal end thereof interior of retainer cap 34. The O-ring 40 provides a seal to prevent the compressed gas from escaping outwardly past needle support 32 during usage of atomizer device 10.

A positive pressure relief port 45 is provided in a portion of valve housing 33 adjacent to O-ring 40 and extends downward to ambient air, which allows a percentage of compressed gas to escape prior to atomization. This permits proper gas-flow adjustments and settings to be made prior to the actual atomization of the liquid, and dramatically reduces the compressed gas operating pressure to an acceptable working pressure.

The trigger valve system 30 is designed to provide enhanced control over the flow of compressed gas to improve control over the spray discharged from atomizer device 10. During operation, the further needle support 32 is depressed inwardly, the greater the flow of compressed gas to nozzle 23, resulting in greater spray pattern intensity. Thus, the trigger valve system 30 provides enhanced control over the spray pattern discharged from atomizer device 10.

While atomizer device 10 as shown in FIG. 1 is configured for use by a right-handed person, discharge section 15 and coupling portion 16 can be reconfigured for use by a left-handed person. This can be accomplished by reversing the placement of liquid outlet tube 18 and gas outlet tube 20 with respect to container 12, and using an appropriate left-hand coupling portion.

In a method of operating the atomizer device 10 for directing a liquid into or on the body of a patient, a source of compressed gas is attached to atomizer device 10 via connecting tube 29. The atomizing nozzle 23 is placed in a preselected position in the body of the patient such as in the nose or mouth. The atomizer device 10 is actuated by depressing push-button 48 inwardly, which dislodges needle valve 36 from conical valve channel 31. This results in needle valve 36 releasing the compressed gas from gas inlet tube 28, with the compressed gas bypassing needle valve 36 and passing through gas channel 21 to nozzle 23. The passage of compressed gas through nozzle 23 withdraws liquid 13 from container 12 through liquid outlet tube 18 into nozzle 23 by a venturi effect such that the liquid is atomized when mixed with compressed gas in the nozzle. The atomized liquid is then discharged in the form of a spray from outlet aperture 25 of nozzle 23 into or on the body of the patient. When push-button 48 is released, needle valve 36 is returned to the closed position toward cap 34 by compression spring 38 and a pneumatic force exerted on needle support 32 by the reduced gas pressure.

The components of the atomizer device of the present invention can be made from various plastic materials or glass materials, which allows the atomizer device to be disposable after use. Nonlimiting examples of suitable plastic materials include polyethylene, acrylonitrile-butadiene-styrene (ABS), polycarbonates such as Lexan, etc. Various combinations of the above materials may be utilized in producing the atomizer device as long as the materials have acceptable physical and mechanical properties.

The various components of the atomizer device of the invention can be manufactured by typical molding techniques known to those skilled in the art. One preferred technique is injection molding of a plastic material. The molded components can then be assembled together to form the atomizer device by standard bonding techniques such as adhesive bonding, ultrasonic welding, and the like. For example, the component parts can be bonded together with an organic adhesive such as methyl ethyl ketone (MEK).

The atomizer device of the present invention provides many benefits and advantages over prior atomizers. Unlike prior devices, the container holding the liquid to be atomized can be sealed to the atomizer device without use of a gasket at the interfacing surfaces. The atomizer device provides for a varying spray pattern control due to the finger/thumb controlled valving arrangement. In addition, the present invention is particularly advantageous over prior devices that use pulling valves, in that only one hand is needed to actuate the trigger valve system of the present atomizer device. Further, the atomizer device of the invention can be made of less expensive materials and is easier to manufacture than prior devices made of metallic components.

The unique trigger valve system of the present invention provides enhanced control in order to generate a particular spray necessary to treat a certain condition. The trigger valve system provides a controlled flow of compressed gas that allows for a varying spray pattern to be generated and discharged from the device, from a gentle spray or mist up to a strong spray as needed. The adjustable nozzle tip of the device allows a liquid medication to be sprayed in various directions as desired. The atomizer device also has the benefit of being a closed system that reduces microbacteria flora, and prevents spreading of infection to a patient and an operator.

The atomizer device of the invention can be used in a hospital, such as in an intensive care unit, operating room, or in a physician's office. Use of the present atomizer device eliminates the possibility of cross-contamination from one part of a medical facility such as a hospital to another part, since the atomizer device is completely disposable and designed for a one-time patient use. Thus, disinfecting or sterilizing the device is not necessary, and there is no need for an autoclave to be used. This eliminates the need for quality control of processed equipment, and breakage of devices from reprocessing is also eliminated.

The atomizer device of the present invention is also easy to use by an operator. In use, the bottle or container is unscrewed from the coupling portion of the device, is filled with the medication of choice, and then screwed back onto the device. Tubing is then connected from an air or oxygen flow meter nipple to the gas inlet tube on the device. The gas flow is then adjusted to the desired setting. This can be accomplished during the static state of the atomizer device due to the pressure relief port located near the vicinity of the O-ring seal. If more gas flow is required, the flow setting can be increased, while if less flow is desired, the flow setting can be decreased. The nominal gas pressure desirable is 50 psi, which is a typical hospital wall outlet pressure, with a flow rate of up to 15 Lpm. The atomizer device is then held at a desired distance with respect to the body of a patient and the flow control push-button is depressed inwardly to produce a spray. In order to increase the spray flow rate from the device, the push-button is depressed further inwardly. In order to decrease the spray flow rate, the pressure applied on the push-button by an operator is reduced. Releasing the push-button automatically shuts off the flow of gas to the atomizer device and allows line pressure to be reduced through the pressure relief port. After use, the atomizer device is disposed of properly, since the device is intended to be for single patient use.

The atomizer device of the present invention is particularly useful for directing a liquid medication or cleaner into or on the body of a patient to treat a variety of medical conditions. The atomizer device can be used to clean and/or medicate various body orifices, such as the mouth, nasal opening, vagina, rectum, or ear. The atomizer device is particularly useful as a nose and throat sprayer for either oil or water base solutions. For example, during use, the nozzle of the atomizer device can be placed in a nasal passage or throat of a patient, and one or more liquid medicaments is then sprayed from the atomizer device to treat a medical condition.

The atomizer device can also be used to treat various conditions located in the buccal, sublingual, pharyngeal, or esophageal areas of oral mucosal tissues. Further, the atomizer device can be used to treat lung/respiratory infections by placing the nozzle into the esophagus of a patient and spraying an appropriate medication. In addition, the atomizer device may also be used to apply a local anesthetic to an area to be treated in or on the body of a patient.

The atomizer device of the invention can also be utilized to apply a liquid medication to an area to be treated on the body of a patient, such as to lesions, abrasions, open wounds, burn areas, and decubitus ulcers. For example, the atomizer device may be used to provide soothing relief to pain receptors by applying a pain-reducing medication such as an analgesic to an area to be treated. The atomizer device may also be used to spray an appropriate liquid in order to soften dressings to be removed from wound areas.

Although the atomizer device of the invention has been described in particular with respect to use for medical purposes, it will be appreciated that the atomizer device can be used for discharging any appropriate liquid in the form of a spray as desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An atomizer device, comprising:
   (a) means for holding a liquid;
   (b) an atomizing nozzle in communication with the means for holding a liquid and a gas outlet tube; and
   (c) a trigger valve system for providing controlled release of compressed gas to the atomizing nozzle, the trigger valve system including a tapered needle valve positioned in a needle support surrounded by a valve housing with a cap, the needle valve slidably disposed in a valve channel in the valve housing and in substantially coaxial alignment with the gas outlet tube the valve housing having a pressure relief port in communication with the valve channel, the needle support being movably engaged with the cap for retaining the needle valve within the valve housing, the needle valve being resiliently biased toward the cap;
   wherein when the needle support is depressed inwardly, the needle support seals the pressure relief port while the needle valve releases the compressed gas to flow through the valve channel into the gas outlet tube and to the atomizing nozzle, thereby withdrawing the liquid into the atomizing nozzle such that the liquid is atomized when mixed with the compressed gas in the atomizing nozzle.

2. The atomizer device of claim 1, wherein the means for holding a liquid comprises a container.

3. The atomizer device of claim 2, wherein the container is made of a plastic material or glass.

4. The atomizer device of claim 2, further comprising a liquid inlet tube disposed in the container.

5. The atomizer device of claim 1, wherein the atomizing nozzle is made of a plastic material.

6. The atomizer device of claim 1, wherein the atomizing nozzle is pivotably attached to the device.

7. The atomizer device of claim 4, further comprising a liquid outlet tube providing communication between the liquid inlet tube and the atomizing nozzle.

8. The atomizer device of claim 1, further comprising a gas inlet tube that is releasably attachable to a source of compressed gas.

9. The atomizer device of claim 8, wherein the gas outlet tube provides communication between the gas inlet tube and the atomizing nozzle.

10. The atomizer device of claim 1, wherein the trigger valve system further comprises an O-ring surrounding a portion of the needle support interior of the valve housing.

11. The atomizer device of claim 1, wherein the needle valve is resiliently biased toward the cap by a compression spring, and by a pneumatic force exerted on the needle support by reduced gas pressure.

12. The atomizer device of claim 1, wherein the device is a closed system that prevents spreading of infection to the patient and an operator.

13. The atomizer device of claim 1, wherein the trigger valve system provides a controlled flow of compressed gas that allows for a varying spray pattern to be discharged from the device, from a gentle spray up to a strong spray as needed.

14. A disposable atomizer device for directing a liquid into or on the body of a patient, comprising:

(a) a container for holding a liquid;

(b) a liquid inlet tube disposed in the container;

(c) an atomizing nozzle in communication with the liquid inlet tube and a gas outlet tube;

(d) a gas inlet tube in communication with the gas outlet tube, the gas inlet tube releasably attachable to a source of compressed gas; and (e) a trigger valve system adjacent to the gas inlet tube for providing controlled release of compressed gas from the gas inlet tube to the atomizing nozzle, the trigger valve system including a tapered needle valve positioned in a needle support surrounded by a valve housing with a cap, the needle valve slidably disposed in a valve channel in the valve housing and in substantially coaxial alignment with the gas outlet tube, the needle support being movably engaged with the cap for retaining the needle valve within the valve housing, the needle valve being resiliently biased toward the cap, the valve housing having a pressure relief port in communication with the valve channel;

wherein when the needle support is depressed inwardly, the needle support seals the pressure relief port while the needle valve releases the compressed gas from the gas inlet tube to flow through the valve channel into the gas outlet tube and to the atomizing nozzle, thereby withdrawing the liquid from the container into the atomizing nozzle such that the liquid is atomized when mixed with the compressed gas in the atomizing nozzle.

15. The atomizer device of claim 14, wherein the container is made of a plastic material or glass.

16. The atomizer device of claim 14, wherein the atomizing nozzle is made of a plastic material.

17. The atomizer device of claim 14, wherein the atomizing nozzle is pivotably attached to the device.

18. The atomizer device of claim 14, further comprising a liquid outlet tube providing communication between the liquid inlet tube and the atomizing nozzle.

19. The atomizer device of claim 14, wherein the trigger valve system further comprises an O-ring surrounding a portion of the needle support interior of the valve housing, and a flow control push-button formed on the needle support exterior of the valve housing.

20. The atomizer device of claim 14, wherein the needle valve is resiliently biased toward the cap by a compression spring, and by a pneumatic force exerted on the needle support by reduced gas pressure.

21. The atomizer device of claim 14, wherein the device is a closed system that prevents spreading of infection to the patient and an operator.

22. The atomizer device of claim 14, wherein the trigger valve system provides a controlled flow of compressed gas that allows for a varying spray pattern to be discharged from the device, from a gentle spray up to a strong spray as needed.

23. A method for directing a liquid into or on the body of a patient, comprising the steps of:

(a) selecting an atomizer device comprising:

(i) a container holding a liquid;

(ii) an atomizing nozzle in communication with the container and a gas outlet tube; and (iii) a trigger valve system for providing controlled release of compressed gas to the atomizing nozzle, the trigger valve system including a tapered needle valve positioned in a needle support surrounded by a valve housing with a cap, the needle valve slidably disposed in a valve channel in the valve housing and in substantially coaxial alignment with the gas outlet tube, the needle support being movably engaged with the cap for retaining the needle valve within the valve housing, the needle valve being resiliently biased toward the cap, the valve housing having a pressure relief port in communication with the valve channel;

(b) connecting a source of compressed gas to the atomizer device;

(c) placing the atomizing nozzle in a preselected position in or near the body of a patient;

(d) depressing the needle support to seal the pressure relief port and release the compressed gas to flow through the valve channel into the gas outlet tube and to the atomizing nozzle, thereby withdrawing the liquid from the container into the atomizing nozzle; and (e) discharging the liquid in the form of a spray into or on the body of the patient.

24. The method of claim 23, wherein the container is made of a plastic material or glass.

25. The method of claim 23, wherein the atomizing nozzle is made of a plastic material.

26. The method of claim 23, wherein the withdrawn liquid passes through a liquid outlet tube providing communication between a liquid inlet tube and the atomizing nozzle.

27. The method of claim 23, wherein the released compressed gas passes through the gas outlet tube providing communication between a gas inlet tube and the atomizing nozzle.

28. The method of claim 23, wherein the needle valve is resiliently biased toward the cap by a compression spring that contracts when the needle support is depressed, and by a pneumatic force exerted on the needle support by reduced gas pressure.

29. The method of claim 23, wherein the liquid comprises one or more medicaments.

30. The method of claim 29, wherein the medicaments can be used to treat a condition on the body of the patient selected from the group consisting of a lesion, an abrasion, a wound, a burn, and a decubitus ulcer.

31. The method of claim 29, wherein the medicaments can be used to treat a condition in the body of the patient located in oral mucosal tissues selected from the group consisting of buccal, sublingual, pharyngeal, and esophageal areas.

32. The method of claim 29, wherein the medicaments are selected from the group consisting of an analgesic, and a local anesthetic.

33. The method of claim 23, wherein the nozzle is placed into a body orifice of the patient selected from the group consisting of a mouth, a nasal opening, a vagina, a rectum, and an ear.

34. The method of claim 23, wherein the nozzle is placed into the esophagus of the patient in order to treat a lung or respiratory infection.

35. The method of claim 23, wherein the liquid is discharged onto a wound dressing in order to soften the dressing prior to removal thereof.

36. The method of claim 23, wherein the atomizer device is a closed system that prevents spreading of infection to the patient and an operator.

37. The method of claim 23, wherein the depressed needle support provides a controlled flow of compressed gas that allows for a varying spray pattern to be discharged from the device, from a gentle spray up to a strong spray as needed.

* * * * *

UNITED STATES PATENT AND TRADEMARK OFFICE
CERTIFICATE OF CORRECTION

PATENT NO. : 6,021,776
DATED : Feb. 8, 2000
INVENTOR(S) : George Allen Allred; Leland J. Coleman; John K. Bullock; Cecil C. Brewer It is certified that error appears in the above-identified patent and that said Letters Patent are hereby corrected as shown below:

Cover Page, U.S. Patent Documents, please insert the following:

4,231,973        Young et al.
        4,343,304        Hickmann
        5,318,015        Mansonn et al.

Col. 4, line 63, change "aproximal" to --a proximal--

Col. 5, line 37, after "at the" change "reward" to --rearward--

Col. 8, line 54, after "tube" insert a comma

Signed and Sealed this

Twenty-fourth Day of April, 2001

Attest:

NICHOLAS P. GODICI

Attesting Officer        Acting Director of the United States Patent and Trademark Office